United States Patent
Harris (10) Patent No.: US 6,680,028 B1
(45) Date of Patent: Jan. 20, 2004

(54) PORTABLE AIR PURIFIER APPARATUS AND SYSTEM

(75) Inventor: Charles D. Harris, Farmers Branch, TX (US)

(73) Assignee: Clean Air Research & Engineering, Inc., Carrollton, TX (US)

(*) Notice: Subject to any disclaimer, the term of this patent is extended or adjusted under 35 U.S.C. 154(b) by 0 days.

(21) Appl. No.: 09/456,346

(22) Filed: Dec. 8, 1999

Related U.S. Application Data (63) Continuation of application No. 08/968,767, filed on Oct. 30, 1997, now abandoned, which is a continuation-in-part of application No. 08/772,081, filed on Dec. 20, 1996, now abandoned, which is a continuation of application No. PCT/US95/07835, filed on Jun. 20, 1995, now abandoned, which is a continuation of application No. 08/262,637, filed on Jun. 20, 1994, now abandoned.

(51) Int. Cl.[7] .................................................. A61L 9/20
(52) U.S. Cl. ........................ 422/122; 55/350.1; 55/472; 55/485; 55/522; 96/114; 96/117; 96/132; 96/153; 96/224; 96/226; 96/381; 96/384
(58) Field of Search .......................... 422/24, 120, 121, 422/122; 55/318, 350.1, 471, 472, 485, 522, 524; 96/114, 115, 117, 109, 132, 135, 153, 224, 226, 381, 384

(56) References Cited

U.S. PATENT DOCUMENTS

| | | |
|---|---|---|
| 2,638,644 A | 5/1953 | Rauhut |
| 3,299,620 A | 1/1967 | Hollingworth |
| 3,802,168 A | 4/1974 | Deckas |
| 3,804,942 A | 4/1974 | Kato et al. |
| 4,118,191 A | 10/1978 | Bohnensieker |
| 4,244,712 A | 1/1981 | Tongret |
| 4,653,384 A | 3/1987 | Amano |
| 4,737,173 A | 4/1988 | Kudirka et al. |
| 4,789,388 A | 12/1988 | Nishibata et al. |
| 4,810,269 A | 3/1989 | Stackhouse et al. |
| 4,909,986 A | 3/1990 | Kobayaski et al. |
| 5,042,108 A | 8/1991 | Yamazumi et al. |
| 5,042,997 A | 8/1991 | Rhodes |
| 5,160,517 A | 11/1992 | Hicks et al. |
| 5,185,015 A | 2/1993 | Searle |
| 5,192,342 A | 3/1993 | Baron et al. |
| 5,203,989 A | 4/1993 | Reidy |
| 5,230,723 A | 7/1993 | Travis et al. |
| 5,240,487 A | 8/1993 | Kung |
| 5,288,298 A | 2/1994 | Aston |
| 5,288,469 A | 2/1994 | Skalla |
| 5,302,354 A | 4/1994 | Watvedt et al. |
| 5,322,473 A | 6/1994 | Hofstra et al. |
| 5,330,722 A | 7/1994 | Pick et al. |
| 5,871,567 A * | 2/1999 | Covington et al. ............ 96/58 |

FOREIGN PATENT DOCUMENTS

| | | |
|---|---|---|
| JP | 2135108 | 5/1990 |
| JP | 3221113 | 9/1991 |

OTHER PUBLICATIONS

"Make Your Home's Air Quality Top Priority with the Climatizer by Healthway," ad, Texaco Marketing Center, Jun., 1994.

* cited by examiner

*Primary Examiner*—Elizabeth McKane
(74) *Attorney, Agent, or Firm*—Crutsinger & Booth (57) ABSTRACT

A portable air purifier system and apparatus which includes a multi-element filter pack that is replaceable as a single unit, thus facilitating health safety of maintenance personnel. By serially disposing filter elements in order of descending sizes of particulates, filtering is improved. Selectably includable within the filters are materials that are particularly efficacious in removing contaminants such as acetone, ammonia, ozone, carbon monoxide, carbon dioxide, ethanol, methane, ethane, methanol, formaldehyde, hydrogen sulfide and other hazardous substances. By including an ultra-violet light source directed onto an activated charcoal layer, germicidal action is facilitated, and noise is abated through the advantageous employment of an expanded plenum and multiple right angle bends in air passageways.

7 Claims, 6 Drawing Sheets

PORTABLE AIR PURIFIER APPARATUS AND SYSTEM

CROSS-REFERENCE TO RELATED APPLICATION

This is a continuation application of U.S. application Ser. No. 08/968,767 filed Oct. 30, 1997, now abandoned, which is a continuation-in-part of U.S. application Ser. No. 08/772,081 filed Dec. 20, 1996, now abandoned, which is a continuation of International Application Serial No. PCT/US95/07835 filed Jun. 20, 1995, now abandoned, which in turn was a continuation of U.S. application Ser. No. 08/262,637 filed Jun. 20, 1994, now abandoned.

TECHNICAL FIELD

This invention relates to air purification systems and more particularly to such systems that are both portable and relatively high in capacity.

BACKGROUND OF INVENTION

The importance of clean air is well known and has increasingly become the subject of governmental and private concern. A variety of illnesses and other physical ailments can be traced directly to air that is impure or contaminated from a variety of industrial and other pollutants generated by human activity. Moreover, other ailments are known to result from air that contains naturally occurring impurities such a bacteria, viruses, mold spores, pollen, dust and the like. Such naturally occurring air impurities are especially likely to be present in sick rooms, hospitals, doctor's offices and other areas where persons with illnesses may congregate.

Not only are there a wide range of ailments experienced by persons having normal immune and allergy profiles, but there are others whose immune or allergic responses, having been weakened by one type of air contaminant, require an especially high degree of protection from other impurities. Accordingly, there have been proposed a variety of systems and devices whose purpose is to provide a clean and wholesome environment in a localized area by removal of sometimes highly concentrated contaminants from immediately surrounding air. Advantageously such systems are self-contained except for a primary energy source, compact and easily portable.

Illustrative or prior proposals are those set forth in U.S. Pat. No. 3,299,620 granted to C. E. Hollingsworth Jan. 24, 1967; U.S. Pat. No. 4,244,712 granted to Stewart Tongret Jan. 13, 1981; U.S. Pat. No. 4,737,173 granted to Paul Kudirka Apr. 12, 1988; U.S. Pat. No. 4,810,269 granted to Wyman Stackhouse et al Mar. 7, 1989; and U.S. Pat. No. 5,230,723 granted to Terrell Travis et al Jul. 27, 1993. These patents disclose portable room air treatment and filtering systems some of which include sequential filtering, sanitization and noise reduction. However, there has continued to be a need for further improvements in mobility, air circulation capacity, safety in use, filter life and maintenance, enhanced protection of personnel when filter changes are needed, reduction in size and noise, and increased flexibility in targeting troublesome contaminants.

BRIEF SUMMARY OF INVENTION

The proposals of the present invention envision an improved air purification unit with high volume air flow, durability, effectiveness in contaminant removal, and ease of operation and maintenance. The system further features very low-noise operation making it especially useful in hospitals and sick rooms where occupants may be easily disturbed and in classrooms and other small assembly areas where noisy operation could disturb the primary function being conducted in the area. It embodies an air purification system housed within a molded polyethylene material for protection against denting and rough handling during movement of the unit or injury to cleaning and maintenance personnel; and it is mounted on four neoprene casters for ease of roll on carpet or vinyl flooring. It includes a retractable power cord, a multi-speed blower with manual, automatic and timer-activated controls, a control panel with a "replace filter module" indicator and an ultra-violet light condition indicator. A unitary four-element disposable filter pack is provided to facilitate filter replacement while minimizing exposure of maintenance personnel to hazardous substances that may have become entrained therein, bacterial growth is inhibited through the provision of an ultra-violet light positioned to irradiate a predetermined exterior surface of the filter module; noise is minimized through the utilization of an air expansion plenum and an air channel labyrinth to and "double-convex" louvers in the exit grill to muffle air and fan sounds. Direction of air exit to facilitate circulation of the filtered air is provided by two-way adjustability of the louvered exit grill. Accordingly, it will be observed that the system includes a plurality of features that act in cooperative combination to achieve an improved air purification system.

OBJECTS AND FEATURES OF THE INVENTION

It is one general object of the invention to provide improved mobile air purification systems.

It is another objective of the invention to provide a mobile air purification system featuring improved convenience of cleaning and maintenance.

It is yet another object of the invention to provide facilitated filter choice and replacement.

It is still another object of the invention to facilitate easy maintenance thereby decreasing exposure of users and maintenance personnel to hazardous substances.

It is still another object of the invention to provide for optional unattended operation for substantial periods of time.

It is a still further object of the invention to provide substantially reduced operational noise by means of multiple noise-reduction techniques.

It is an even further object of the invention to provide an air purification system using a uniquely constructed multi-stage unitary filter.

Accordingly, the invention features a smooth molded polyethylene housing, large neoprene casters and a retractable power cord, thus improving ease of movement and safety in cleaning and use.

In accordance with another feature of the invention, an improved control system is provided to control a multi-speed blower and to provide a visual display when system filters or ultra-violet lights require servicing, thus enhancing system operation.

In accordance with still another feature of the invention, an improved filter construction facilitates creation of custom multi-element unitary filter packs that are tailored to the particular environmental conditions in which the system is to be employed, thereby improving purification effectiveness and ease of use.

In accordance with yet another feature of the invention, an air expansion plenum is employed in cooperative combination with the multi-speed blower, right-angled air passages shaped exit grill louvers, thus contributing top enhanced noise reduction.

These and other objects and features of the invention will be apparent from the following detailed description, by way of preferred examples, with references to the drawings.

DETAILED DESCRIPTION OF THE INVENTION

Figure 1:
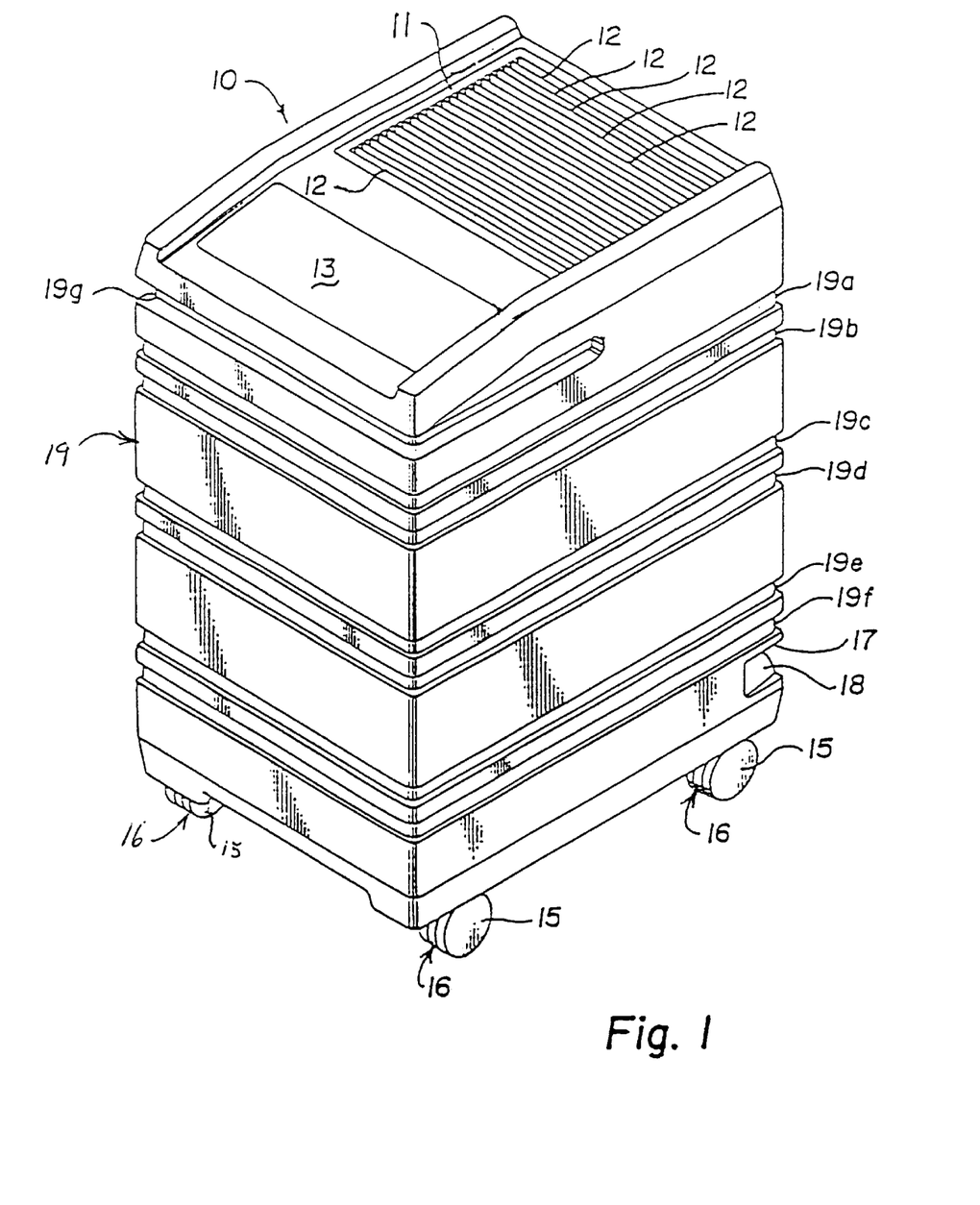
FIG. 1 is a perspective view depicting a preferred embodiment of the portable air purifier according to the invention hereof.

Now, turning to the drawing, and more particularly to FIG. 1 thereof, it will be seen to depict the air purifier according to the invention, indicated generally at 10. In the top surface of the unit there is mounted an adjustable air exit grill 11 which includes a plurality of louvers 12 rotatably adjustable about their longitudinal axes so as to direct the flow of exit air. Preferably the louvers 12 are connected into two groups of about half the louvers each so that half of the louvers may be directed together in one direction and the other half in the same or another direction for optional circulation of air in the immediate area. Also mounted in the top surface is visual display panel 13 including display instruction and touch sensitive control areas as described in connection with FIG. 5. These areas provide for displaying various operating conditions and for setting/operating controls including turning the unit on/off, setting it to the aforementioned auto-timing or manual modes, re-setting the internal timer to the correct time of day, and providing for setting on and off times when controls are in the auto-timing mode. The display panel 13 is made of easily cleanable Mylar material, is touch sensitive and includes a user instructions read-out which can be followed to activate selected touch-sensitive locations on the panel face. It also includes an easily readable back-lighted display that includes a digital clock which not only displays the time of day but also includes an indication of when the system filter pack needs to be replaced. Also included is an indicator identifying the on/off condition of the ultra-violet sanitizing light and when it needs to be replaced.

The exterior case 19 is formed of conventional but smoothly molded polyethylene material in whose surface there are formed grooves 19a–19g which serve not only to add ornamental attractiveness but more importantly to add strength, thus reducing the material thickness required and contributing to the relatively light-weight character of the equipment.

With further reference to FIG. 1 neoprene casters 15, which have relatively large bearing surfaces areas 16, are provided for ease of movement of the air purifier over floor surfaces such as carpeting. At the lower right hand side of unit 10 is located a recess 17 in which the plug and a retractable power cord 18 rests when the cord is not in use.

Figure 2:
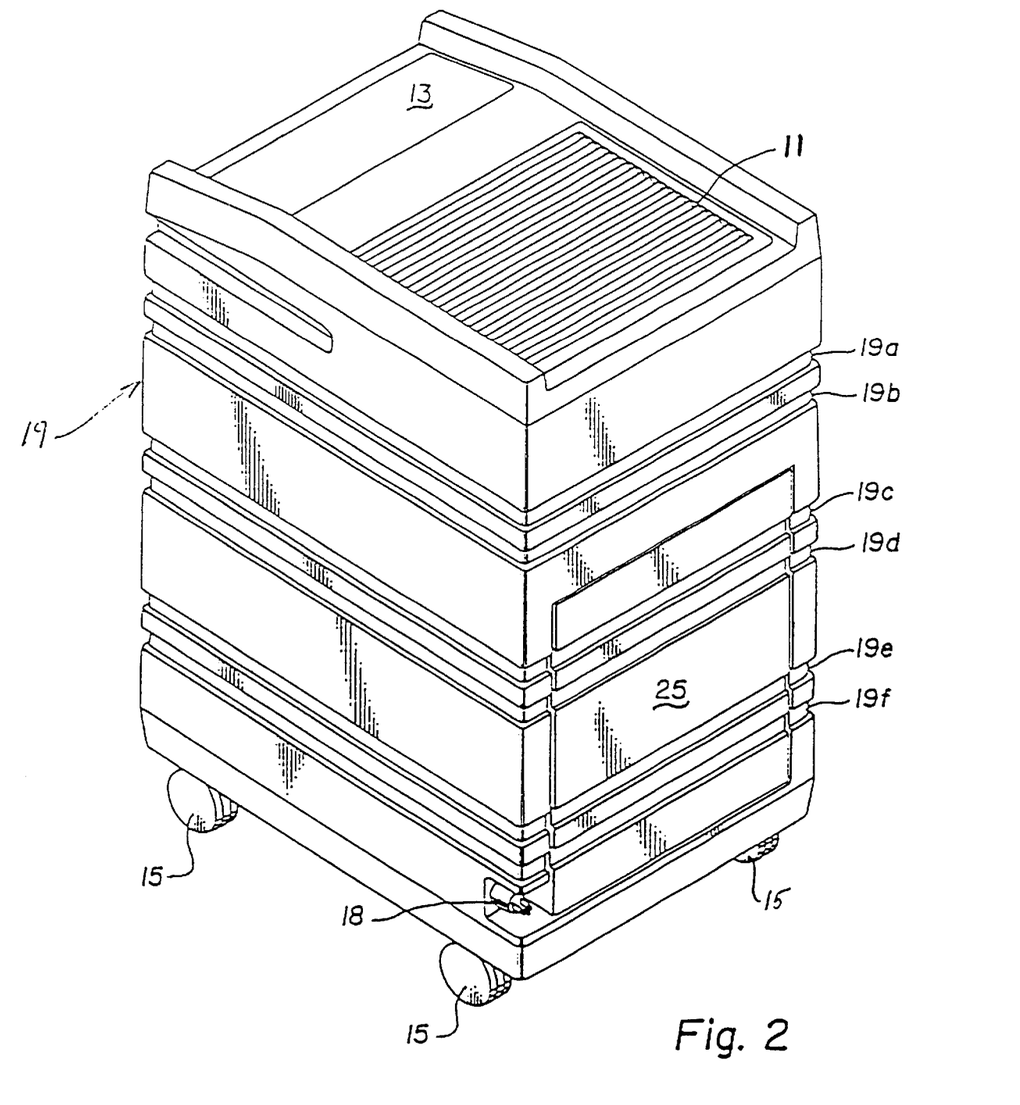
FIG. 2 is another perspective view taken from the right rear of the unit of FIG. 1.

As mentioned above, FIG. 2 is a perspective view taken from the right rear of the unit. There, in addition to elements shown in FIG. 1, there is also shown a detachable filter access door 25. Although filter access door 25 could be attached in any of a number of ways, in accordance with the preferred embodiment hereof, it is fitted on its inside surface with conventional flat spring clips (not shown) which engage with adjacent surfaces of the main cabinet housing 19 so that a gentle tug on the door 25 releases it for disengagement. When it is desired to reinstall the door, it is gently pressed into place and the spring clips re-engage the adjacent surfaces of the housing to hold it in place against a sealing gasket, not shown.

Figure 3:
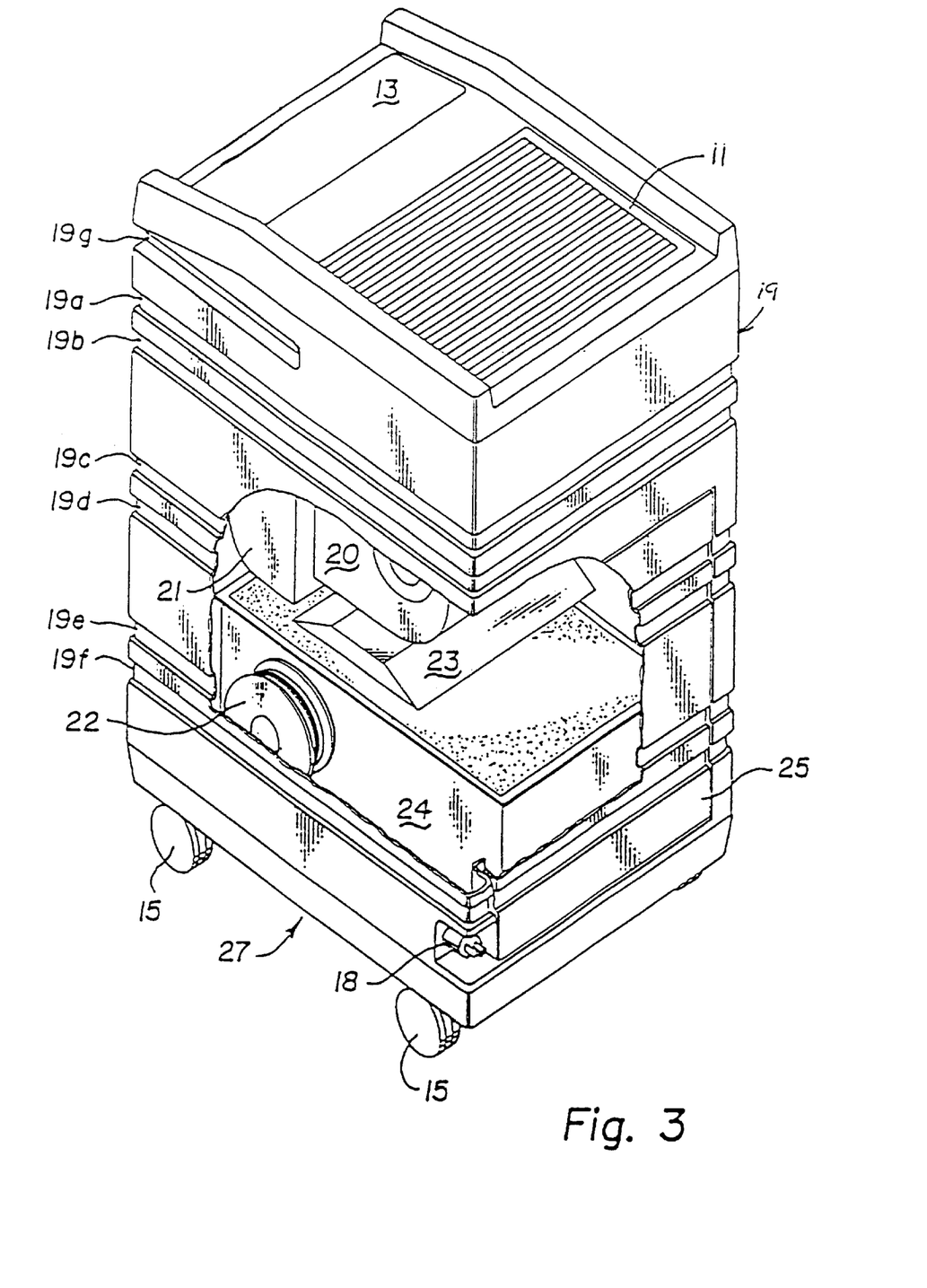
FIG. 3 is another perspective view of the preferred embodiment partly cut away to reveal internal components.

Now turning to FIG. 3, it will be seen to depict another perspective view of the preferred embodiment partly cut away to reveal internal components. Mounted within the casing 19 it will be observed are a conventional multi-speed motor-blower 20; an air plenum chamber 21 which is connected between the output of motor-blower 20 and air exit grill 12; an electrical cord retrieval take-up spool 22; a germicidal ultra-violet light assembly 23; and a multi-stage filter pack 24. Also shown are the filter access door 25 and the air intake region 27 which resides in the lower surface of case 19 between the supporting neoprene casters 15 (see also FIG. 4).

As mentioned above, FIG. 4 is a side sectional view of the portable air purifier. There, shown are motor-blower 20, air plenum chamber 21, ultra-violet light source 28 within its reflector 29 which reflects ultra-violet light downwardly to the top surface 30 of unitary filter pack 24 as indicated by dashed lines 31. The ultra-violet light assembly 23 may be seen to further include a detector 26 mounted within the reflector 29 to monitor the strength of the radiation from ultra-violet light 28 to indicate when there is need to replace the ultra-violet light 28. Adjacent the bottom of the unit there is provided a rack 32 which may optionally be used to position a screen or very course pre-filter at the discretion of the user. Although provided for user convenience, it is contemplated that a separate screen or pre-filter will be used rarely, if at all.

From further inspection of FIG. 4, it will be observed that, in operation of the unit, air is drawn into the unit through region 27 below the filter unit 24 whence it passes through filter unit 24 into the interior cabinet chamber area 33 which in the preferred embodiment is about five cubic feet in volume. By providing such a relatively spacious interior volume, air passage noise is reduced. Next, the air is drawn into the intake of the motor-blower 20 whence it is discharged into plenum chamber 21. Chamber 21 also is intentionally enlarged so that the air expands and slows down, thereby further reducing air flow noise. After passing through chamber 21, the air (represented by curved arrow 35) is then directed through a motor-blower noise-reducing semi-labyrinthine passageway 34 having softly curved interior surfaces (e.g., 34a–34c) to further reduce air movement noise before exiting through the aforementioned adjustable louvers 12. Accordingly, though an efficacious combination of chamber sizes and passageway geometries, the unit operates very quietly.

Figure 5:
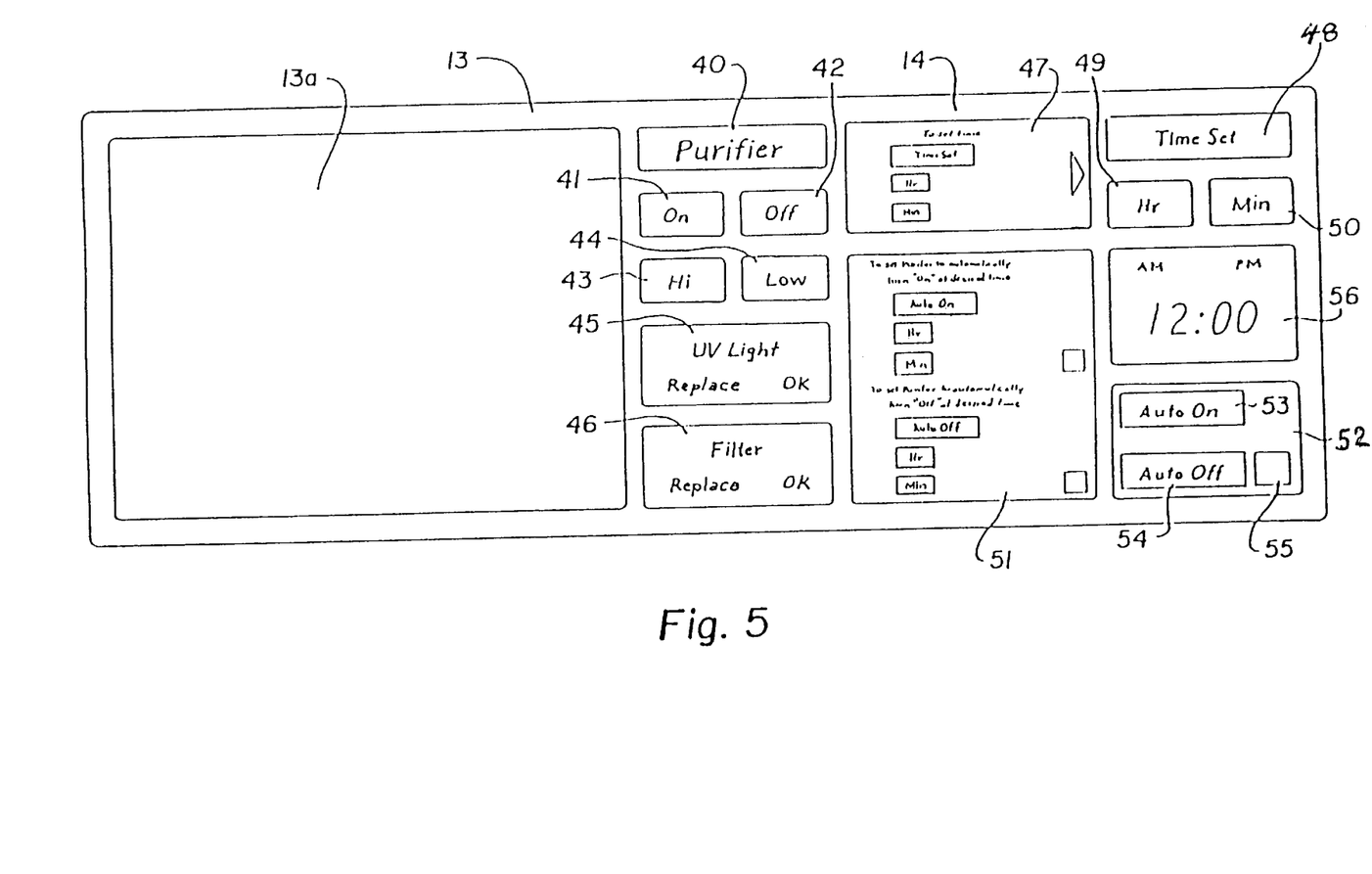
FIG. 5 is a view depicting the control and display panel of the portable air purifier.

FIG. 5 depicts the above-mentioned visual display panel 13 in greater detail. As mentioned previously, the touch-sensitive control areas 14 of the panel include a variety of features and controls that are of particular benefit in operating the air purifier system; whereas, the left side includes region 13a on which items such as nameplates, special messages or other indicia may be displayed. From the previous description it will be recalled that designated areas provide for displaying various operating conditions and for setting/operating controls including turning the unit on/off, setting it to the aforementioned auto-timing or manual modes, setting the time of the internal timer to the correct time of day, and providing for setting on and off times when controls are in the auto-timing mode. The display panel is made of easily cleanable Mylar material, and is conventionally touch sensitive at designated touch-sensitive locations on the panel face. It also includes an easily readable back-lighted digital clock which not only displays the time of day but also includes an indication of when the system filter pack needs to be replaced. Also included is an indicator identifying the on/off condition of the ultra-violet sanitizing light and when it needs to be replaced.

Although operation of the controls is believed evident from the legends that appear in FIG. 5, further description is as follows: Item 40 is a conventional nameplate to readily identify the equipment to persons unfamiliar therewith. "On" surface area 41 and "Off" surface area 42 provide for manual turn on and turn off. "Hi" and "Low" surface areas 43 and 44 make provision for two speed operation of the motor-blower. Area 45 is back-lighted with a light that comes on when loss or reduction of ultra-violet light radiation indicates a need for bulb replacement or other servicing. Area 46 is similarly back-lighted with a light that comes on when pressure across the filter pack 24 rises to a level indicative of a need for servicing or replacing the filter.

As will be evident to those skilled in the art, any of a variety of conventional ultra-violet light sensors may be employed to detect the absence or low-emission of the ultra-violet light and thereby to activate back-lighted region 45. In addition, it will be evident to those skilled in the art that as substances are filtered (removed) from the air, the flow of air through filter pack 24 will tend to become impeded, thereby raising the pressure differential across the filter pack. Such pressure differential is readily correlatable with filter condition such that when the filter pack needs to be serviced or replaced, a predetermined pressure differential will have been attained. In accordance with the preferred embodiment hereof, the pressure differential across the filter pack is conducted through conventional latex tubing to a PSF101 ultra low pressure switch as supplied by World Magnetics Company of Traverse City, Mich. There, when the differential pressure builds to a level indicative of an excess of particulate matter in the filter, contacts on the switch operate to activate the "replace filter" indicator 46.

Before returning to further description of the unit controls, it may be helpful to note that the purpose of the ultra-violet light is to de-contaminate the upper surface of the filter pack 24 which, in the preferred embodiments contains activated charcoal. Since, if not de-contaminated, micro-organisms may flourish in the activated charcoal surface, it is desirable to destroy such organisms both from the standpoint of maintaining purity of air and perhaps more importantly, to protect servicing personnel that might otherwise be exposed when changing filters.

It will also be evident to those skilled in the art that any of a variety of conventional ultra-violet light sources may be employed for source 28. However, one particularly useful unit has been found to be in the Germicidal Ultra-violet lamp as supplied by the American Ultraviolet Company of Santa Ana, Calif. This unit produces ultra-violet light ninety percent of which is at a wavelength of approximately 253.7 nm, a mercury spectral line known in the art as "Germicidal Radiation" because of its destructive effects on DNA and consequent destruction of micro-organisms. With the above-identified light, an average bacterium will be killed in about ten seconds at a distance of six inches.

Now returning to FIG. 5, it will be observed that the right hand section 14 of panel 13 additionally includes instruction area 47 which is adjacent to the time set area 48, touch sensitive hour setting area 49 and touch sensitive minute setting area 50. In addition, there is included an auto timing instruction area 51 which is adjacent to auto set region 52 which includes touch sensitive "auto on" setting area 53, "auto off" setting area 54 and "set" area 55; and rounding out the right hand portion 14 of panel 13 is the aforementioned set-time and time-of-day display 56. As will be observed, areas 47 and 51 include detailed instructions on setting time of day and well as automatic on and off operation as desired.

As previously mentioned, one of the features of the apparatus and system is its provision for customizing filter packs. In accordance with the preferred embodiment, each filter pack may be comprised of up to four distinct filter elements, thus offering a variety of filter combinations tailored to the particular use for which the equipment is intended. Moreover, since filter packs are easily exchangeable, flexibility is normally achieved through a simple substitution of one filter pack for another.

Figure 6:
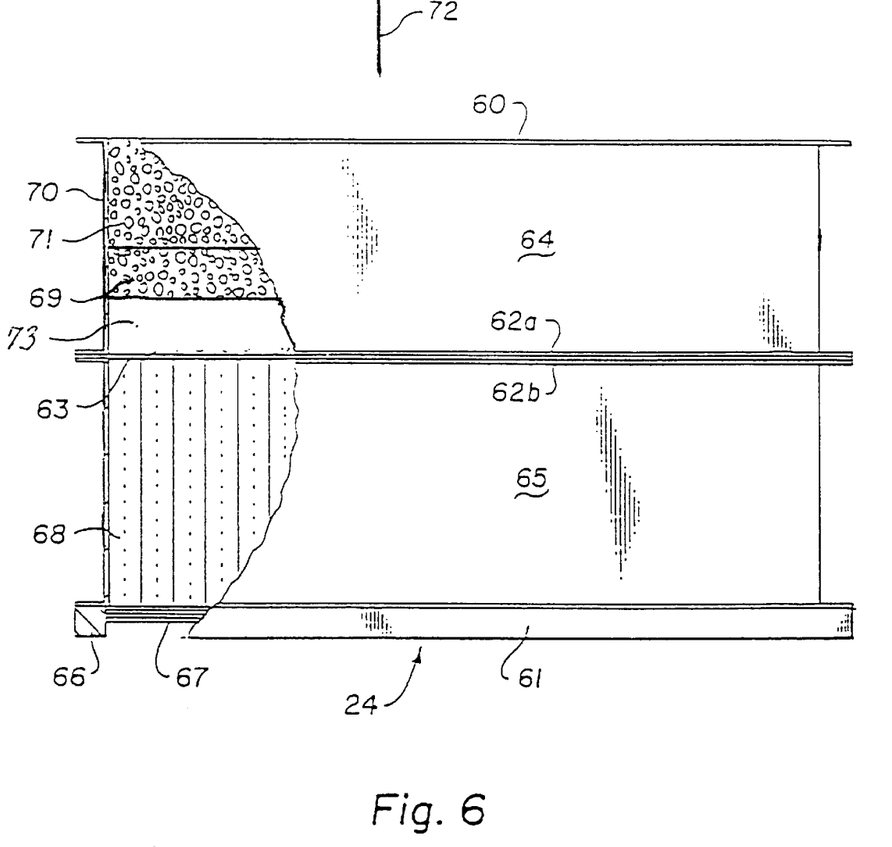
FIG. 6 is a partially sectioned view depicting filter packs according to the invention and illustrating their adaptability to customizing.

FIG. 6 is a partially cut away view through a filter pack 24 constructed in accordance with the invention. There, it will be observed are upper and lower frame members 60 and 61 which may be any one of a variety of conventional materials from which filter frames are ordinarily constructed. Lying horizontally and approximately mid-way from top to bottom are joining members 62a and 62b which adjoin separator 63 (preferably including gauze material) which separates the upper and lower parts 64 and 65. Near the lower extremity is a peripheral gasket 66. An electrostatic pre-filter is indicated by 67. Gasket 66 may be made of a variety of conventional materials, and electrostatic pre-filter 67 may be any one of a variety of conventional filters generally available on the commercial market. However, in accordance with the preferred embodiment hereof, the pre-filter preferably is 3M Company's Filtrete brand filter. This filter has been found effective in trapping mold spores and bacteria in the three micron range.

The direction of air flow through filter pack 24 is from the bottom toward the top, and therefore, air first passes through the electrostatic pre-filter 67 where relatively large pollutants are removed. The air then passes upwardly into H.E.P.A. filter 68 in the second section of the filter pack. As will be recognized by those skilled in the art, H.E.P.A. stands for the designation "High Efficiency Particulate Apparatus," a standard identification in the industry. In the preferred embodiment hereof, H.E.P.A. filter section 68 is comprised of about 40 square feet surface area of micro glass folded into 3/8 inch pleats. H.E.P.A. filters of this type are known for their particulate holding capabilities in the 0.1 micron range. An example of such filter section is the well known "HEPA-PLEAT II" filter supplied by Applied Air Filter Company of San Jose, Calif. After passing through separator 63, the air enters a third filter stage section 69 which is optionally comprised of any one of three different agents, depending upon the use to which the equipment is put: (1) for odor control of substances such as formaldehyde, it is charged with potassium permanganate; (2) for order control of chlorine and acetic acid, it is charged with potassium hydroxide; and (3) for odor control of ammonia it is charged with phosphoric acid. Examples of such are those of the UNISORB brand of products manufactured by the Unisorb Corporation of South Houston, Tex. These products include the foregoing agents together with activated zeolite(s) and/or activated alumina.

It has been found that in filters of the type preferred for use in the odor-control section filter 69, the filter material granules tend to separate and allow formation of conduit paths through which air can flow without being properly filtered. Such conduits tend to form starting in surface regions of slightly higher pressure resulting from uneven flow of air from the adjacent H.E.P.A. filter. As a feature of the present invention conduit formation in the filter element 69 is substantially eliminated by providing a pressure equalization space 73 between filter element 68 and filter element 69. The equalization space 73 need only provide a separation between filter element 68 and 69 of about ¼" or more to be effective.

It will be evident to one skilled in the art that due to the ease of filter pack replacement, an operator could easily select any one of three different filter packs severally including elements (1), (2) or (3) in the third section, depending upon the principal odor-producing substances encountered in the environment of use. In addition, it is contemplated that a filter pack housing could be provided with a slidably removable third stage section 69 so as to provide for flexibility and customization of use for the foregoing and other odor-producing substances. In such event, materials other than those enumerated above could be employed in section 3.

After passing through the third section filter 69, the air, now essentially free of powerful odors, moves through fourth section 70 in which remaining, or trace odors, are removed by activated coconut charcoal 71. As is known to those skilled in the art, activated coconut charcoal is particularly efficacious in removing most noxious odors, although it is known to have an inherent tendency to encourage bacterial growth, the aforementioned ultra-violet light is provided to direct bacterial-killing ultra-violet light directly onto the upper surface of the filter pack 24 and prevent bacterial growth.

Although a variety of activated charcoals may be utilized in practicing the principles of the invention, it has been found that a particularly effective type is the activated coconut charcoal that is sold under the brand name "Unicarb AC" by the aforementioned Unisorb Corporation. In the four-element filter pack hereof, the activated coconut charcoal is rendered particularly effective by the fact that by the time the air reaches it, most of the contaminants and odors have already been removed, thus permitting the charcoal to operate at or near optimum efficiency.

After passing through the four section filter pack, the air exits in a generally upward direction as represented by arrow 72. It moves into the interior region 33 (FIG. 4), and thence as described above.

Figure 4:
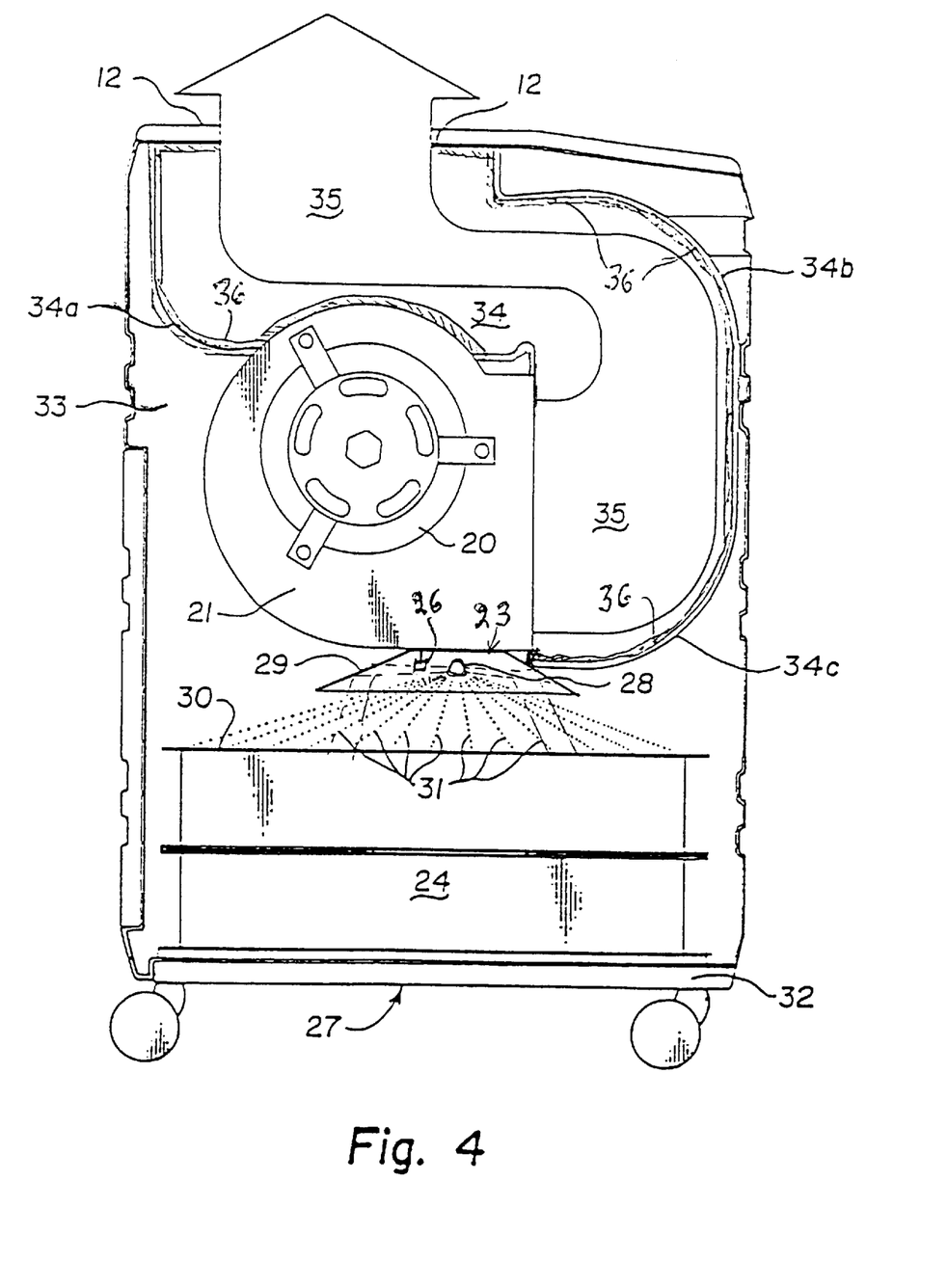
FIG. 4 is a sectional view of the portable air purifier.

As a further means of operational noise reduction in the unit, the walls of passageway 34 may be lined with a layer of anti-bacterial foam-like material as indicated at 36 in FIG. 4. The layer need by only a few millimeters thick but because it is relatively soft and porous in nature the layer is very sound-absorbative and thus further reduces the noise resulting from air movement through the unit. Anti-bacterial form is preferred in order to prevent or retard any bacterial growth in the foam.

As air exits the unit through the grill 11 as directionally deflected by louvers 12 there is a potential for noise generation due to the turbulence of air from the deflection. In the present filter unit noise generated by the louvers 12 is significantly reduced by the shape of the louvers 12.

Figure 7:
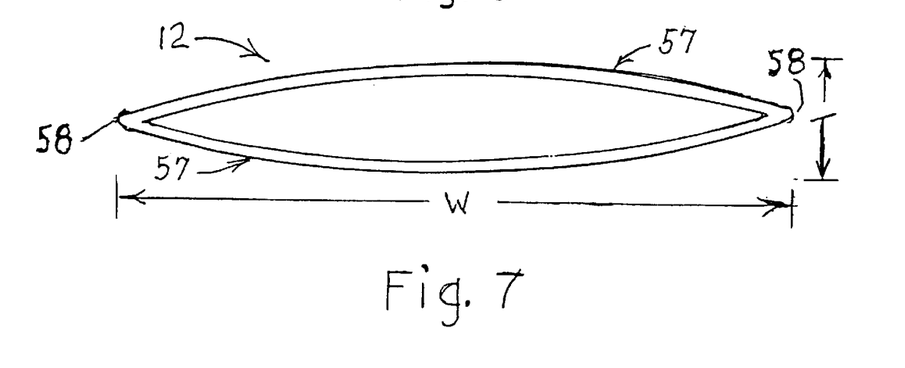
FIG. 7 is an end view, in section, of one of the louvers of the air exit grill.

Shown in FIG. 7 is an end view in section of a louver 12 suitable shaped to reduce turbulence noise and air exiting the air purifying unit through grill 11. As can be seen, each louver 12 is generally symmetrical with a pair of convex surfaces 57 converging to relatively sharp or narrow leading/trailing edges 58. Although the louver is shown to be hollow and made of sheet-like plastic, metal or other suitable material, it may be made as a solid piece. However constructed it is to be of sufficient strength and rigidity that it will not vibrate from the air flow over it when in use. The suitable width to thickness ratio (W/T) of a suitable louver will, of course, dependent on various factors such as the type and weight of material from which the louver is made, the maximum velocity of the air expected to pass over the louver and the unsupported length of the louver within the grill 11.

It will now be evident to those skilled in the art that there has been described herein an improved air purifier system having a number of features and advantages including utilization of ultra-violet light to extend filter life, quiet operation, flexibility and effectiveness, ease of deployment, adaptability for a variety of environments and simplicity in operation and control.

Although the invention hereof has been described by way of example of a preferred embodiment, it will be evident that other adaptations and modifications can be employed without departing from the spirit and scope thereof. For example, an additional section could be added to the unitary four-pack filter if expected environmental conditions warranted such addition.

The terms and expressions employed herein have been used as terms of description and not of limitation; and thus, there is no intent of excluding equivalents, but on the contrary it is intended to cover any and all equivalents that may be employed without departing from the spirit and scope of the invention.

Having described the invention, I claim:

1. A portable air purifier system comprising in combination:

(a) a housing having a bottom surface defining an air inlet opening and a top surface defining an air outlet opening and control means for controlling said system;

(b) a plenum means disposed within said housing;

(c) a plurality of walls within said housing defining a multidirectional air passage between said plenum means and said outlet opening;

(d) a multiple section unitary filter pack disposed within said housing over and covering said air inlet opening;

(e) a motor/blower means disposed within said housing for drawing air from the ambient through said inlet opening and said filter pack and exhausting essentially all air thus drawn into said plenum means and thence through said air passage and through said outlet opening back into said ambient external of said housing;

(f) means for sensing the differential pressure across said multiple section unitary filter back and indicating when said differential pressure reaches an unacceptable level;

(g) ultraviolet radiation means for preventing bacterial growth on the external air exit surface of said multi-section unitary filter pack;

(h) an ultraviolet radiation sensor positioned to receive ultraviolet radiation from said ultraviolet radiation means and indicator means to provide indication of a lowering of germicidal effectiveness of said ultraviolet radiation to an unacceptable level; and (i) an antibacterial foam material lining the interior surface of said walls defining said multidirectional air passage.

2. The air purifier system of claim 1 wherein the multiple-section unitary filter pack comprises a first section electrostatic filter, a second section H.E.P.A. filter, a third section filter of a granular particle bed comprised of materials selected from the group consisting of potassium permanganate, potassium hydroxide, phosphoric acid, a mixture of any two of said materials and a mixture of all three of said materials, and a fourth section filter comprised of a particle bed of activated charcoal.

3. The air purifier system of claim 1 wherein said third section particle-bed is further comprised of activated alumina.

4. The air purifier system of claim 3 wherein said third particle bed is further comprised of activated zeolite.

5. The air purifier system of claim 3 wherein said second section filter and said third section filter are separated by an air space of at least ¼ inch.

6. The air purifier system of claim 3 wherein said multidirectional air passage embodies at least three smoothly curved 90° bends.

7. The air purifier system of claim 1 wherein said walls defining said multidirectional air passage embody at least three smoothly curved 90° bends in said air passage.

* * * * *